United States Patent [19]

Keegan et al.

[11] 3,936,402

[45] Feb. 3, 1976

[54] ANHYDROUS PRODUCTS HAVING IMPROVED WETTABILITY CHARACTERISTICS, CASE 5

[75] Inventors: James J. Keegan, Bloomfield; Girish Patel, Mine Hill; Howard Rubin, Rockaway, all of N.J.

[73] Assignee: Warner-Lambert Company, Morris Plains, N.J.

[22] Filed: Dec. 9, 1974

[21] Appl. No.: 530,579

Related U.S. Application Data

[63] Continuation-in-part of Ser. No. 302,162, Oct. 30, 1972, Pat. No. 3,878,138.

[52] U.S. Cl............ 260/17 R; 106/35; 260/DIG. 36
[51] Int. Cl.$^2$............................................ C08L 1/28
[58] Field of Search........... 260/DIG. 36, 17 R, 231, 260/897 B, 94.9 CD; 106/35

[56] References Cited
UNITED STATES PATENTS

| | | | |
|---|---|---|---|
| 3,003,988 | 10/1961 | Germann et al. | 260/33.6 |
| 3,427,191 | 2/1969 | Howell et al. | 117/138.8 |
| 3,472,840 | 10/1969 | Stone et al. | 260/231 |
| 3,736,274 | 5/1973 | Schoenholz et al. | 260/17 R |
| 3,833,518 | 9/1974 | Rubin et al. | 260/17 R |

OTHER PUBLICATIONS

Kanner et al., *Chemical Abstracts*, 67:12,857f (1967).

Bailey et al., *Chemical Abstracts*, 70:79;407q (1970).

*Primary Examiner*—Donald E. Czaja
*Assistant Examiner*—W. C. Danison, Jr.
*Attorney, Agent, or Firm*—Albert H. Graddis; Frank S. Chow; Anne M. Kelly

[57] ABSTRACT

Water-wettable anhydrous products, such as the powders and creams used in cosmetic and drug products, are admixed with 20 to 60% by weight, based on the weight of the total formulation, of a powdered polyethylene or powdered polypropylene polymer, to improve wettability characteristics. Denture adhesive powders prepared from an anionic/cationic adhesive combination, together with the powdered polyethylene or polypropylene polymer display particularly improved properties. The polyethylene or polypropylene polymer may also be admixed with other anhydrous products including dentifrices, vaginal powder sprays, and the like. Low molecular weight polyethylene powder, with an average molecular weight of from 1,000 to 3,500, is suitable for use in products of the invention. For the polypropylene, a molecular weight of from 120,000 to 350,000 is specified. The powdered polymers have a particle size of less than 422 microns.

5 Claims, No Drawings

ANHYDROUS PRODUCTS HAVING IMPROVED WETTABILITY CHARACTERISTICS, CASE 5

CROSS REFERENCE TO RELATED APPLICATION

This application is a continuation-in-part of United States Ser. No. 302,162, filed Oct. 30, 1972, now U.S. Pat. No. 3,878,138.

BACKGROUND OF THE INVENTION

Many cosmetic and drug products are formulated as anhydrous powders and creams to protect the particular ingredients in the formulation as well as for convenience in manufacturing, packaging, storage and handling. However, since most of these products depend upon water for actual utility, any difficulties encountered in wetting the preparation at the time of use greatly detract from the overall consumer acceptance of the product.

Such is the case with many anhydrous dental preparations including denture adhesives, dentifrices, and the like. Similar problems are frequently encountered with products such as anhydrous vaginal powder spray formulations.

It has now been found that the addition of a powdered polyethylene or polypropylene polymer to such anhydrous powder and cream preparations greatly enhances the wettability characteristics of the preparation.

SUMMARY OF THE INVENTION

Anhydrous powder and cream formulations containing from 20 to 60% by weight, based on the total weight of the preparation, of a powder polyethylene or a powdered polypropylene polymer having a particle size of less than 422 microns, have superior wettability characteristics. Suitable polyethylene powders are of low molecular weights, i.e., from about 1,000 to 3,500; polypropylene powders having higher molecular weights, i.e., from 120,000 to 350,000 are used. A particularly preferred product is a denture adhesive powder containing about 10% by weight of a cationic copolymer of acrylamide with $\beta$-methacryloyloxyethyltrimethyl ammonium methyl sulfate; about 40% by weight of sodium carboxymethyl cellulose; and about 50% by weight of a powdered polyethylene polymer having an average molecular weight of about 2,000 or about 50% by weight of a powdered polypropylene having an average molecular weight of about 140,000.

DESCRIPTION OF THE INVENTION

This invention relates to anhydrous powder and cream preparations which contain a powdered polyethylene or a powdered polypropylene polymer to provide improved wettability characteristics.

The powdered polyethylene polymers suitable for use in the practice of this invention have an average molecular weight ranging from about 1,000 to 3,000, preferably from about 2,000 to 2,500, and a particle size of less than about 422 microns, preferably between about 74 to 149 microns. The particle size may also be stated in terms of the mesh size, i.e., not larger than 40 mesh, preferably between about 100 to 200 mesh. Powdered polyethylene polymers having an average molecular weight of about 2000 and a particle size of about 74 microns (200 mesh) are especially preferred.

As representative of polyethylene polymers falling into the above-described category, there may be mentioned the waxy reaction products of ethylene with isopropanol, produced according to the processes described in U.S. Pat. Nos. 2,504,400, 2,712,534, and 2,683,141, wherein there is obtained a telomer product having the formula below, with $n$ being 3 to 150:

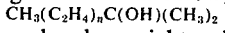

$$CH_3(C_2H_4)_nC(OH)(CH_3)_2$$

Low molecular weight polymers obtained in this manner are subjected to a pulverizing after-treatment, using a cryogenic-pulverizing process, if necessary, to obtain a powdered polyethylene product of the desired particle size.

As examples of commercially available powdered polyethylene products suitable for use in this invention, there may be mentioned those sold by Allied Chemical Company, Morristown, New Jersey, under the name A-C Polyethylene 6A, A-C Polyethylene 8A, A-C Polyethylene 9A, A-C Polyethylene 6AF, A-C Polyethylene 8AF, and A-C Polyethylene 9AF. Similarly, powdered polyethylene products sold by United Stated Industries, Park Avenue, New York 10017, as their Microthene series are also suitable.

Powdered polypropylene polymers suitable for use in the practice of this invention have an average molecular weight ranging from about 120,000 to 350,000, preferably about 120,000 to 160,000, and a particle size of less than about 422 microns, preferably between about 74 to 149 microns. Powdered polypropylene polymers having an average molecular weight of about 140,000 and a particle size of about 74 microns are especially preferred. As representative of polypropylene polymers falling into the above-described category, there may be mentioned polypropylene homopolymers prepared by the various polymerization techniques described in Encyclopedia of Chemical Technology, Vol. 14: pages 292-296, 1967, John Wiley & Sons, Inc., i.e., using a Ziegler-Natta catalyst and controlling the molecular weight in order to achieve the desired molecular weight. The polypropylene polymer obtained is pulverized to obtain a powdered material having a particle size suitable for use in the practice of this invention.

As an example of commercially available powdered polypropylene homopolymers which improve the water-wettability of powders and creams according to the teachings of this invention, there may be mentioned those sold by Hercules, Inc., Wilmington, Delaware, as the Hercoflat series.

The above-described powdered polyethylene or powdered polypropylene, when incorporated into various anhydrous powder and cream formulations, has been found to impart vastly superior wettability characteristics to final products when they are wet with water. The exact reason for this improvement is not thoroughly understood, but is thought to possibly involve the coating of the individual polyethylene particles with one or more hydrophilic ingredients in the anhydrous powder or cream, thus affording improved accessibility of hydrophilic surfaces to the wetting fluid.

Representative anhydrous powder and cream formulations which are substantially improved by the addition of the above-described polyethylene or polypropylene powders include denture adhesives, dentifrices, vaginal powder sprays, and similar cosmetic and drug products. Superior wettability characteristics are obtained in these anhydrous cosmetic and drug products by the addition of about 20 – 60% by weight, preferably about 20 – 55% by weight, based on the weight of the total formulation, of the polyethylene or polypropylene powders, according to the teaching of this invention.

As an example of a product which is particularly improved by the incorporation of the aforementioned polyethylene or polypropylene powders, there may be mentioned a denture adhesive powder formulated to contain, as the adhesive, a mixture of a cationic polymeric component and an anionic natural or synthetic component which, when applied to dentures and exposed to moisture, develops adhesive properties. Such a denture adhesive product is described in U.S. application Ser. No. 243,816, filed Apr. 13, 1972, now U.S. Pat. No. 3,833,518, and in U.S. application Ser. No. 476,742, file June 5, 1973, now U.S. Pat. No. 3,868,339. In the denture adhesive described in aforementioned patent applications, the cationic polymeric component is at least one O-lower alkyl-trimethylammonium chloride-substituted-anhydroglucose polymer described generally in United Stated Patent No. 3,742,480 as having the formula:

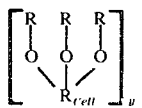

wherein $R_{Cell}$ is the residue of an anhydroglucose unit, $y$ is an integer having a value of from about 50 to about 20,000, and each R individually represents a substituent group of the general formula:

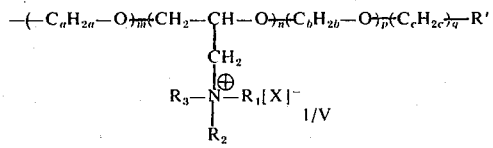

wherein:
a is an integer having a value of from 2 to 3;
b is an integer having a value of from 2 to 3;
c is an integer having a value of from 1 to 3;
m is an integer having a value of from zero to 10;
n is an integer having a value of from zero to 3;
p is an integer having a value of from zero to 10;
q is an integer having a value of from zero to 1;
R' is a member selected from the group consisting of

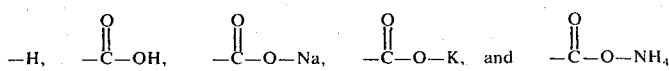

with the proviso that when $q$ is zero then R' is —H;

$R_1$, $R_2$ and $R_3$, taken individually, represent a member selected from the group consisting of alkyl, aryl, aralkyl, alkaryl, cycloalkyl, alkoxyalkyl and alkoxyaryl radicals where each of $R_1$, $R_2$ and $R_3$ can contain up to 10 carbon atoms, with the proviso that when said number is an alkoxyalkyl radical there are at least 2 carbon atoms separating the oxygen atom from the nitrogen atom, and with the further proviso that the total number of carbon atoms in radicals represented by $R_1$, $R_2$ and $R_3$ is from 3 to 12 with the further proviso that when $R_1$, $R_2$ and $R_3$ are taken together the nitrogen atom to which $R_1$, $R_2$ and $R_3$ are attached can be a component of a heterocyclic ring selected from the group consisting of pyridine, α-methylpyridine, 2,5-dimethylpyridine, 2,4,6-trimethylpyridine, N-methyl-piperidine, N-ethyl piperidine, N-methyl morpholine and N-ethyl morpholine; X is an anion;

V is an integer which is equal to the valence of X; the average value of n per anhydroglucose unit of said cellulose ether is from about 0.01 to about 1; and the average value of m+p+q per anhydroglucose unit of said cellulose ether is from about 0.01 to about 4.

In the aforementioned formula for the cationic polymer, preferred cationic polymers for use in the denture adhesive of this invention are obtained when $y$ is an integer having a value of from about 1000 to about 5000 and each R individually represents a substituent group of the general formula:

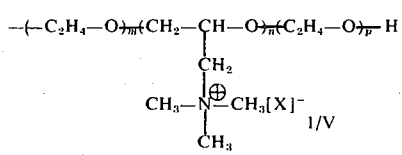

wherein:
m is an integer having a value of from zero to 10;
n is an integer having a value of from zero to 3;
p is an integer having a value of from zero to 10;
X is an anion;
V is an integer which is equal to the valence of X; the average value of n per anhydroglucose unit of the cellulose ether is from 0.01 to 1; and the average value of m+p per anhydroglucose unit of the cellulose ether is from 0.01 to 4.0.

Especially preferred cationic polymers are those in which X is chlorine, the average value of n per anhydroglucose unit of the cellulose ether is from 0.1 to 0.5, and the average value of m+p per anhydroglucose unit of the cellulose ether is from 0.1 to 2.5. A particularly preferred O-alkyl-trimethylammonium chloride-substituted-anhydroglucose polymer of this type is commercially available as Polymer JR-400 from Union Carbide Corporation, New York, New York. Polymer JR-400 is water soluble and, at a concentration of 1% and a temperature of 25°C, yields a solution having a viscosity of 400 centipoises.

As the anionic ingredient of the denture adhesive, there may be used one or more synthetic gums which are copolymers of maleic acid with vinyl-lower alkyl-ether having from 1 to 5 carbon atoms in the lower alkyl group.

Maleic acid/vinyl-alkyl-ether copolymers are described in U.S. Pat. No. 2,047,398, patented July 14, 1936 and in U.S. Pat. No. 2,782,182, patented on Feb. 19, 1957. The alkyl group in the vinyl ether may contain from 1 to 5 carbon atoms. Suitable lower alkyl vinyl ether monomers include methyl vinyl ether, ethyl vinyl ether, divinyl ether, propyl vinyl ether, isobutyl ether and the like. Polymerization techniques used to obtain these copolymers are those well known in the art, i.e., utilizing appropriate proportions of monomers and reaction conditions. The mole ratio of the total of ether monomers to the total of maleic anhydride is substantial unity: polymerization of one mole of alkyl vinyl ether with one mole of maleic anhydride. This anhydride copolymer should be hydrolyzed to the free acid form for use in the denture adhesive of this invention; monovalent, alkali metal salts thereof may also be used. Copolymers of this type have been found to be gum-like and have anionic characteristics and may therefore be used as the anionic component in the denture adhesive of this invention.

Among the suitable anionic materials described above, one or more of the synthetic gums marketed commercially as GANTREZ HY be General Aniline and Film Corp., New York, N.Y., 10020 have been found to be especially effective in the denture adhesive of this invention. These gums are poly(methyl vinyl ether/maleic acid) compounds having a specific viscosity of from 1 to 8.

An improved denture adhesive powder containing the above-described ingredients, together with polyethylene or polypropylene powder according to the teachings of this invention is formulated to contain from about 40 to 60% by weight, based on the weight of the total formulation, of the powdered polyethylene or powdered polypropylene; from about 5 to 55% by weight, of at least one of the above-described cationic polymeric materials; and from about 5 to 55% by weight, of at least one of the above-described anionic gums. Preferred products contain from about 45 – 55% by weight, based on the weight of the total formulation of the polyethylene or polypropylene powder; about 5 – 20% by weight, of at least one of the cationic polymeric materials; and from about 20 – 50% be weight, of at least one of the anionic gums. A most preferred product is formulated to contain about 50% by weight, based on the weight of the total formulation of the polyethylene or polypropylene powder, about 10% by weight, of at least one cationic polymeric material, and about 40% by weight, of at least one anionic gum.

Typical dentifrice powder formulations which may be improved by the incorporation of the above-described powdered polyethylene or powdered polypropylene, according to the practice of this invention, are formulated to contain an abrasive material, such as dicalcium phosphate dihydrate or precipitated calcium carbonate, a soap or detergent ingredient, flavors, sweeteners and excipients. Such representative dentifrice powders are described in Remington's Pharmaceutical Sciences, pages 1785–1786, 13th Edition, Mack Publishing Co., Easton, Pa., 1965. In order to obtain improved wettability, according to the teachings of this invention, the powdered polyethylene or powdered polypropylene is incorporated into the dentifrice powder formulation at a level of from about 20 – 60% by weight, based on the total weight of the formulation, preferably about 20 – 50% by weight, most preferably about 45% by weight.

As an example of an anhydrous dentifrice paste, there may be mentioned the toothpaste formulation of U.S. Pat. No. 3,574,824. Improved wettability of the aforementioned anhydrous toothpaste is obtained by the incorporation of the powdered polyethylene or powdered polypropylene, according to the practice of this invention. A typical improved anhydrous toothpaste formulation of this type contains a mineral oil ingredient; a polyethylene glycol composition; a nonionic emulsifier such as Atmos 300 (Atlas Chemical Industries); a binding agent such as polyvinylpyrrolidone; mannitol or inositol; an abrasive, and coloring agents; sweeteners, and the usual excipients, together with from about 20 – 60% by weight, based on the weight of the total formulation, of powdered polyethylene or powdered polypropylene, as described above. Preferred anhydrous dentifrice pastes contain about 20 – 50% by weight, based on the weight of the total formulation, of polyethylene or polypropylene powders; and a most preferred product contains about 20% by weight, based on the total weight of the formulation, of polyethylene or polypropylene powder, to improve wettability characteristics of the anhydrous dentifrice paste. Such modified anhydrous toothpaste formulations demonstrate more thorough cleansing power when applied to the teeth, since wettability characteristics have been greatly improved.

Representative vaginal spray powders which may be improved by the addition of the polyethylene or polypropylene powder according to the practice of this invention generally contain solid ingredients including a lubricant, such as isopropyl palmitate, and talc, together with the desired liquid fragrances and an anhydrous alcohol solvent. Propellants are added as the formulation is placed into the spray container. In order to improve the wettability of vaginal sprays of this type, from about 20 – 60% by weight, based on the total weight of solids in the formulation, of powdered polyethylene or powdered polypropylene is added to the formulation. Preferred products contain from about 20 – 60% by weight of powdered polyethylene or polypropylene, based on the total weight of solids. Particularly preferred products are formulated to contain about 23% by weight of powdered polymer, based on the total weight of solids, in order to provide superior wettability characteristics to the vaginal spray product.

Obviously, many other anhydrous powder and cream preparations in the cosmetic, dental and drug field, other than those specifically mentioned above, could be improved by the addition of the powdered polyethylene or polypropylene according to the practice of this invention.

To further illustrate the invention, the following examples are given:

EXAMPLE 1

Preparation of Improved Denture Adhesive Powder

In a Hobart mixer, add 1950 grams of poly(methyl vinyl ether/maleic acid) and 6.25 grams of peppermint oil, USP. Mix until the ingredients assume a crumbly, dry character and pass through a No. 20 mesh screen. Into a separate blender, add 500 grams of O-lower alkyl trimethylammonium chloride substituted anhydroglucose powder (Polymer JR); and 2543.50 grams of powder polyethylene having an average molecular weight of 2000 and having particle size such that 99.5% of the polyethylene powder passes through a 60 mesh screen. Add in the mixed gum and peppermint oil from the Hobart mixer. Mix all ingredients for 20 minutes or until a uniform blend is obtained. Add in 0.25 grams of F D & C Red No. 3 Aluminum Lake and mix to visual uniformity.

EXAMPLE 2

Preparation of Denture Adhesive Powder

A denture adhesive powder is prepared to contain the following ingredients:

| | |
|---|---|
| Polymer JR | 15.0 pounds |
| Copolymer of methylvinylether and maleic acid | 35.0 pounds |
| Polypropylene powder (60 mesh) | 49.0 pounds |
| Cab-O-Sil M-5 | 1.0 pound |
| Peppermint Oil | 0.1 pound |

The peppermint oil is well dispersed in about 25 pounds of the copolymer of methylvinylether and maleic anhydride.

The Cab-O-Sil M-5 and polypropylene powder are similarly dispersed in the remaining copolymer of methylvinylether and maleic anhydride.

The two premixes are then placed in a ribbon blender mixing apparatus. The whole is mixed for about 15 minutes, after which the 15.0 pounds of the Polymer JR is added and the batch mixed for an additional 15 minutes.

EXAMPLE 3

Preparation of Improved Anhydrous Toothpaste Formulation 255 grams of a mixture polyethylene glycols having average molecular weights of 550, 600, and 4,000, and 50 grams of a propylene glycol bodying agent are mixed and melted at 65°–70°C. Heat is discontinued and 10 grams of polyvinylpyrrolidone is added to the heated mixture which is stirred vigorously to form a uniform slurry (A). In a separate steam-jacketed mixer, 100 grams of mineral oil, 40 grams of a petrolatum bodying agent and 2 grams of Atmos 300 emulsifier (Atlas Chemical Industries) are mixed and heated to a temperature of 50°C. The slurry (A) is added to the ingredients in the steam-jacketed mixer. The following remaining ingredients, after screening (20 mesh screen) are then added to the mixer: 20 grams of sodium lauryl sulfate detergent, 257 grams of hydrated alumina abrasive, 30 grams of aluminum silicate abrasive, 26 grams of mannitol, 10 grams of titanuim dioxide color, and 76 grams of synthetic sweetener. All ingredients are mixed for 20–25 minutes, after which heat is discontinued and the mixture cooled to 30°C. 200 grams of powdered polypropylene having an average molecular weight of about 140,000 and a particle size of approximately 200 mesh, is added together with 20 grams of flavor, and the whole is mixed for an additional 20–25 minutes.

EXAMPLE 4

Preparation of Improved Vaginal Spray Powder

Add 0.5 grams of the isopropyl palmitate and 2.10 grams of a powdered polyethylene having an average molecular weight of about 2000 and a particle size of approximately 200 mesh to 2.5 grams of anhydrous alcohol and mix thoroughly. Add .2 grams of fragrance and blend with other ingredients. Weigh 5 grams of blended ingredients into an aerosol container, add 8.5 grams of talc and pressure fill with 88.2 grams of propellant (40:60 mixture of Propellant 12 and Propellant 114).

Having thus described our invention, we claim;

1. A denture adhesive powder having superior wettability characteristics comprises a substantially anhydrous mixture of nontoxic, adhesive ingredients and from about 40% to about 60% by weight, based on the total weight of the denture adhesive ingredients of a powdered polymeric material having an average particle size of less than about 422 microns, said polymeric material being selected from the group consisting of powdered polyethylene having an average molecular weight ranging from about 1000 to about 3500 and polypropylene having an average molecular weight ranging from about 120,000 to about 350,000, said denture adhesive ingredients comprising:

A. from about 5 to about 55% by weight, based on the total weight of the denture adhesive ingredients of at least one cationic polymeric material having the formula:

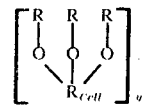

wherein $R_{Cell}$ is the residue of an anhydroglucose unit, $y$ is an integer having a value of from about 1000 to about 5000, and each R individually represents a substituent group of the general formula:

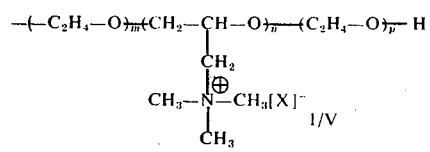

wherein:
    $m$ is an integer having a value of from zero to 10;
    $n$ is an integer having a value of from zero to 3;
    $p$ is an integer having a value of from zero to 10;
    X is an anion; V is an integer which is equal to the valence of X; the average value of $n$ per anhydroglucose unit of said cellulose ether is from about 0.01 to about 1; and the average value to $m+p$ per anhydroglucose unit of said cellulose ether is from about 0.01 to about 4; and B. from about 5% to about 55% by weight, based on the total weight of the denture adhesive, of at least one anionic gum selected from the group consisting of copolymers of maleic acid with vinyl-lower alkyl-ether wherein the alkyl group has from 1 to 5 carbon atoms.

2. A denture adhesive according to claim 1 wherein, in the cationic polymeric material of (A) X is chlorine, the average value of n per anhydroglucose unit of said cellulose ether is from about 0.1 to about 0.5, and the average value of $m+p$ per anhydroglucose unit of said cellulose ether is from about 0.1 to about 2.5.

3. A denture adhesive according to Claim 2 wherein the powdered polymeric material which provides the superior wettability characteristics is present in an amount of from about 45% to about 55% by weight, based on the total weight of the denture adhesive ingredients; said powdered polymeric material having an average particle size of between about 74 to 149 microns and being selected from the group consisting of a powdered polyethylene having a molecular weight of from about 2000 to about 2500, and powdered polypropylene having an average molecular weight of from about 120,000 to about 160,000.

4. A denture adhesive according to claim 3 wherein the anionic gum is selected from the group consisting of copolymers of methylvinylether with maleic acid.

5. A denture adhesive according to claim 4 wherein the anionic gum is a copolymer of methylvinylether with maleic acid.

* * * * *